United States Patent
Lerner (10) Patent No.: US 11,622,905 B2
(45) Date of Patent: Apr. 11, 2023

(54) PROPORTIONAL JOINT-MOMENT CONTROL FOR POWERED EXOSKELETONS AND PROSTHESES

(71) Applicant: Arizona Board of Regents on Behalf of Northern Arizona University, Flagstaff, AZ (US)

(72) Inventor: Zachary F. Lerner, Flagstaff, AZ (US)

(73) Assignee: ARIZONA BOARD OF REGENTS ON BEHALF OF NORTHERN ARIZONA UNIVERSITY, Flagstaff, AZ (US)

( * ) Notice: Subject to any disclaimer, the term of this patent is extended or adjusted under 35 U.S.C. 154(b) by 262 days.

(21) Appl. No.: 16/403,121

(22) Filed: May 3, 2019

(65) Prior Publication Data

US 2020/0179215 A1    Jun. 11, 2020

Related U.S. Application Data

(60) Provisional application No. 62/777,382, filed on Dec. 10, 2018.

(51) Int. Cl.
| | |
|---|---|
| *A61H 3/00* | (2006.01) |
| *A61F 2/70* | (2006.01) |
| *A61H 1/02* | (2006.01) |
| *A61F 5/01* | (2006.01) |

(52) U.S. Cl.
CPC ............ *A61H 3/00* (2013.01); *A61F 2/70* (2013.01); *A61F 5/0123* (2013.01); *A61F 5/0127* (2013.01); *A61H 1/024* (2013.01); *A61H 1/0244* (2013.01); *A61H 1/0266* (2013.01); *A61H 2003/007* (2013.01); *A61H 2201/14* (2013.01); *A61H 2201/1642* (2013.01); *A61H 2201/5007* (2013.01); *A61H 2201/5061* (2013.01); *A61H 2201/5071* (2013.01)

(58) Field of Classification Search
CPC ........ A61H 3/00; A61H 1/024; A61H 1/0244; A61H 1/0266; A61H 2003/007; A61H 2201/14; A61H 2201/1642; A61H 2201/5007; A61H 2201/5061; A61H 2201/5071; A61F 2/70; A61F 5/0123; A61F 5/0127
See application file for complete search history.

(56) References Cited

U.S. PATENT DOCUMENTS

| | | | |
|---|---|---|---|
| 2003/0115031 A1 | 6/2003 | Dariush et al. | |
| 2004/0249316 A1 | 12/2004 | Ashihara et al. | |
| 2008/0319361 A1* | 12/2008 | Messer | A61F 5/0111 602/6 |

(Continued)

*Primary Examiner* — Jerrah Edwards
*Assistant Examiner* — Aren Patel
(74) *Attorney, Agent, or Firm* — Quarles & Brady LLP (57) ABSTRACT

Lower-limb exoskeletons used to improve free-living mobility for individuals with neuromuscular impairment must be controlled to prescribe assistance that adapts to the diverse locomotor conditions encountered during daily life, including walking at different speeds and across varied terrain. This system employs an ankle exoskeleton control strategy that instantly and appropriately adjusts assistance to the changing biomechanical demand during variable walking. Specifically, this system utilizes a proportional joint-moment control strategy that prescribes assistance as a function of the instantaneous estimate of the ankle joint moment.

19 Claims, 8 Drawing Sheets

(56) References Cited

U.S. PATENT DOCUMENTS

| | | |
|---|---|---|
| 2011/0264238 A1* | 10/2011 | van der Merwe ........ A61F 2/54 623/24 |
| 2013/0226048 A1 | 8/2013 | Unluhisarcikli et al. |
| 2014/0100492 A1* | 4/2014 | Nagasaka .............. A61H 3/061 601/34 |
| 2015/0066153 A1* | 3/2015 | Palmer, III ................ A61F 2/70 623/24 |
| 2015/0321342 A1 | 11/2015 | Smith et al. |
| 2016/0143800 A1 | 5/2016 | Hyung et al. |
| 2017/0202725 A1 | 7/2017 | Robertson et al. |
| 2018/0085280 A1* | 3/2018 | Shimada ............ A63B 21/0004 |
| 2018/0177672 A1 | 6/2018 | Uchida et al. |
| 2020/0039061 A1 | 2/2020 | Sankai |

* cited by examiner

PROPORTIONAL JOINT-MOMENT CONTROL FOR POWERED EXOSKELETONS AND PROSTHESES

CROSS-REFERENCE TO RELATED APPLICATION

This application claims priority to U.S. Provisional Application No. 62/777,382 filed on Dec. 10, 2018, the entire contents of which is incorporated herein by reference.

GOVERNMENT FUNDING

This invention was made with Government support under grant number R03 HD094583 funded by the National Institutes of Health and grant number 1756029 funded by the National Science Foundation. The Government has certain rights in the invention.

BACKGROUND

Impairment of the human neuromuscular system, including from amputation, stroke, Parkinson's disease, and cerebral palsy (CP), often leads to lower-extremity impairment and significantly reduced long-term mobility. Despite conventional treatments and walking aids, nearly all affected individuals fail to attain normal function and activity levels. Advances in actuators, power storage, and computing have led to the design and implementation of robot-assisted therapy and mobility. Powered exoskeletons and prostheses designed to increase mobility may augment the ankle joint, because proper ankle function is essential for efficient bipedal walking. Neuromuscular impairment affecting the lower-extremity typically results in reduced ankle push-off during mid-late stance. Many existing wearable robotic assistive devices have exhibited limited or no benefit outside of controlled laboratory environments, with effective control a primary limiting factor.

The control of lower-limb exoskeletons to augment or restore mobility in real-world settings for individuals with neuromuscular impairment remains a critical challenge in the field wearable robotics. Powered exoskeleton and prostheses control strategies capable of improving mobility must adapt to, and transition between, the diverse locomotor conditions encountered during daily life, such as gait initiation, walking at different speeds, and across varied terrain. Additionally, in order to successfully adopt wearable robotic devices into daily life, their control strategies must be adaptable to variable environmental conditions, allow for self-implementation, and maximize ease of use.

A variety of control strategies have been developed for powered exoskeletons and prostheses across a number of walking conditions, yet limitations exist for their practical implementation in real-world settings. The use of electromyography (EMG) signals has been used to distinguish ambulatory conditions. However, in clinical populations, such as CP, muscle spasticity can saturate the volitional neuromuscular control in the EMG pattern. Furthermore, EMG control relies on and is susceptible to changes in electrode-skin conductivity, motion artifact, electrode placement, fatigue, and cross-talk; these challenges pose realistic barriers for using EMG control during daily life. The use of human in the loop optimization, while successful in unimpaired individuals walking in controlled conditions (i.e., treadmill or stair stepper at set speeds), may require relatively lengthy learning periods (120+ minutes), and is not suited for adapting to instantaneous changes in task and for individuals with limited mobility. The use of algorithms to detect a user's intent has demonstrated decent reliability for classifying level walking, sitting, standing, and stair ascent/decent. Yet, intent recognition techniques have limited applicability for clinical populations that exhibit considerable gait variability and progressive ambulatory deterioration. Moreover, the inability or failure to detect completely unique conditions (e.g., irregular walking, stumbling, unforeseen obstacles, unexpected disturbances, etc.) could have dangerous consequences.

Therefore, there is a need for powered exoskeleton and powered prostheses control schemes that automatically adapts assistance across locomotor tasks encountered during daily life, is well-suited for assisting individuals with pathological gait patterns, and is realistic to implement in a real-world setting.

SUMMARY

The present invention provides systems and methods comprising one or more devices configured to apply assistive force across one or more joints of a user.

In an embodiment, a device comprises an orthosis configured to couple to an ankle of a user, a pressure sensor coupled to the orthosis and configured to be positioned underneath a foot of the user when the orthosis is coupled to the ankle of the user, a motor configured to apply a force to the orthosis to generate a torque force in the ankle of the user; and a processor. The processor is configured to receive a force measurement value from the pressure sensor, determine, using the force measurement value, a desired assistive torque value, and operate the motor to cause the motor to apply a force to the orthosis to generate a torque force in the ankle equal to the desired assistive torque value.

In an embodiment, a device comprises an orthosis configured to couple around a body joint of a user, a pressure sensor coupled to the orthosis, a motor configured to apply a force to the orthosis to generate a torque force across the joint of the user, and a processor. The orthosis is configured to be coupled to a first body part on a first side of the joint and a second body part on a second side of the joint. The processor being configured to operate the motor based on a force measurement received from the pressure sensor.

In an embodiment, a method of applying assistive force comprises receiving a force measurement from a pressure sensor to produce a force measurement value, determining, from the force measurement value, a desired assistive torque value, and operating a motor to cause the motor to apply a motor force to the orthosis to generate a motor torque force across the joint equal to the desired assistive torque value. The pressure sensor is configured to measure a force applied by a body part of a user.

DESCRIPTION OF THE DRAWINGS

The drawings described herein constitute part of this specification and includes exemplary embodiments of the present invention which may be embodied in various forms. It is to be understood that in some instances, various aspects of the invention may be shown exaggerated or enlarged to facilitate an understanding of the invention. Therefore, drawings may not be to scale.

DETAILED DESCRIPTION

A powered exoskeleton and powered prostheses control framework may suitably adapt assistance across locomotor tasks encountered during daily life, while also remaining realistic for users to implement themselves while at home. A control strategy may be based on a concept of providing assistance that is proportional to an instantaneous demand (i.e., a net joint moment) placed on a joint (e.g., ankle joint, knee joint, hip joint).

Proportional joint-moment control may be based on a torque balance about a particular joint (i.e., the ankle joint, knee joint, hip joint). A force or pressure sensor may be located between the foot and ground and used to approximate the ground reaction force applied to a proximal segment (e.g., the foot), along with inferred or calculated point of force application (center of pressure).

A mapping function or regression equation may be used to relate a measured force or pressure to an approximation of a biological joint moment. Alternately, measured force or pressure may directly approximate a biological joint moment. A calibration procedure may be used to relate the measured force information to a reference task (e.g., preferred walking speed). An equation or table underlying a mapping function may be generated from data obtained by calibration procedures. During operation, a ratio of an instantaneous estimated joint moment may be computed relative to an estimated joint moment during a reference task. During operation, the absolute instantaneous estimated joint moment may also be calculated. Exoskeleton assistance (torque) may then be provided as a function (e.g. proportional) to a real-time relative or absolute approximation of a joint moment (e.g., torque may be provided as 50% of the estimated biological moment). An exoskeleton assistive torque may adapt instantaneously to a demand placed on a biological joint during a weight-bearing task. A system and method may employ control strategy based on a concept of providing assistance that is related to (e.g. proportional to) the instantaneous demand placed on the ankle joint.

A biological moment (e.g. hip, knee, ankle) may be calculated via a real-time inverse dynamics estimation approach, whereby an estimation of a ground reaction force may be coupled with one or more measurements of a moment arm between a sensor (e.g. a force sensor on a foot) and a joint (e.g. ankle joint). Coupled information from an estimated ground reaction force and one or more additional sensors (e.g. joint angle encoders, inertial measurement units) may be used in an inverse dynamics calculation governed by the equations of motion.

Figure 1:
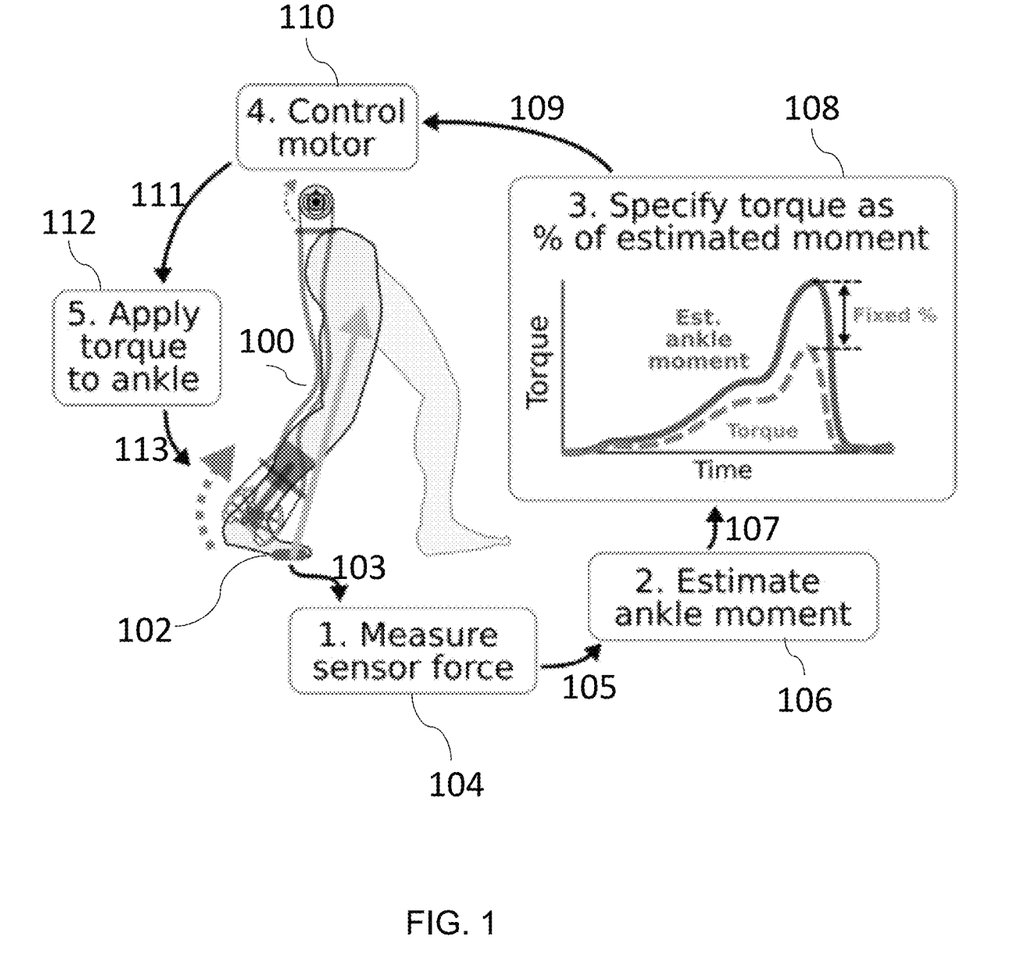
FIG. 1 shows an overview of a method for prescribing exoskeleton assistance that is proportional to a joint moment.

FIG. 1 shows an example process flow diagram for proportional control of an assistive device 100 (e.g. an ankle exoskeleton assistive device) based on data received from a force or pressure sensor 102. One or more sensors 102 may be disposed on assistive device 100 (e.g. force sensors against a foot or inside a shoe) and configured to measure force or pressure with which the wearer's foot pushes against a ground or floor surface. Sensor 102 transmits electrical signals 103 to measurement device 104. Measurement device 104 may interpret sensor electrical signal 103 as measured force or pressure 105, which may include force generated by user and by assistive device 100. Measured force 105 may then be processed with or without a mapping function or regression equation 106 to determine user-generated torque 107. That is, measured force 105 may be translated directly or indirectly into an approximation of the torque force being generated at the user's ankle. User-generated torque 107 may then be multiplied by scaling factor 108 (which may be user-selected) to determine desired assistive torque 109. Desired assistive torque 109 may then be used to control the operation of motor controller 110 (e.g. a proportional-integral-derivative (PID) feedback motor controller), which, in turn, sends motor instructions 111 to motor 112. Specifically, motor 112 is operated to apply assistive torque 113 to the body of the user (e.g. assistive ankle torque) with a force magnitude determined by desired assistive torque 109.

A control strategy, herein denoted as proportional joint-moment control, may be based on a concept of providing assistance that is proportional to an instantaneous demand placed on a biological joint (i.e., a net moment generated by muscles and other biological tissues crossing a joint). This approach may include estimating a user's joint moment in real-time (e.g. via a measurement or assessment of foot-ground reaction force), and prescribing assistive torque as a fixed percentage of the user's joint moment. Exoskeleton assistive torque that is instantaneously (or substantially instantaneously) synchronized with a net muscular demand at a joint may intuitively and safely correspond to a user's intention. Assistive torque synchronized with a measured force (e.g. measured force 105) may correspond to a user's intention. Herein, force sensors and pressure sensors may be considered as equivalent sensors. Given that pressure may be defined as force divided by area, a force measurement and a pressure measurement may differ only by a constant scaling factor of the sensor area.

An approach to estimate an ankle joint moment in real-time may be based on torque balance. Torque balance may approximate torque or net moment produced by muscles (e.g. across the ankle, knee, or hip) by balancing a resultant torque produced by a ground reaction force. Force sensors having an appropriate range of sensitivity may be located under the forefoot and may be used to approximate a ground reaction force along with inferred point of force application (e.g. center of pressure).

Figure 2:
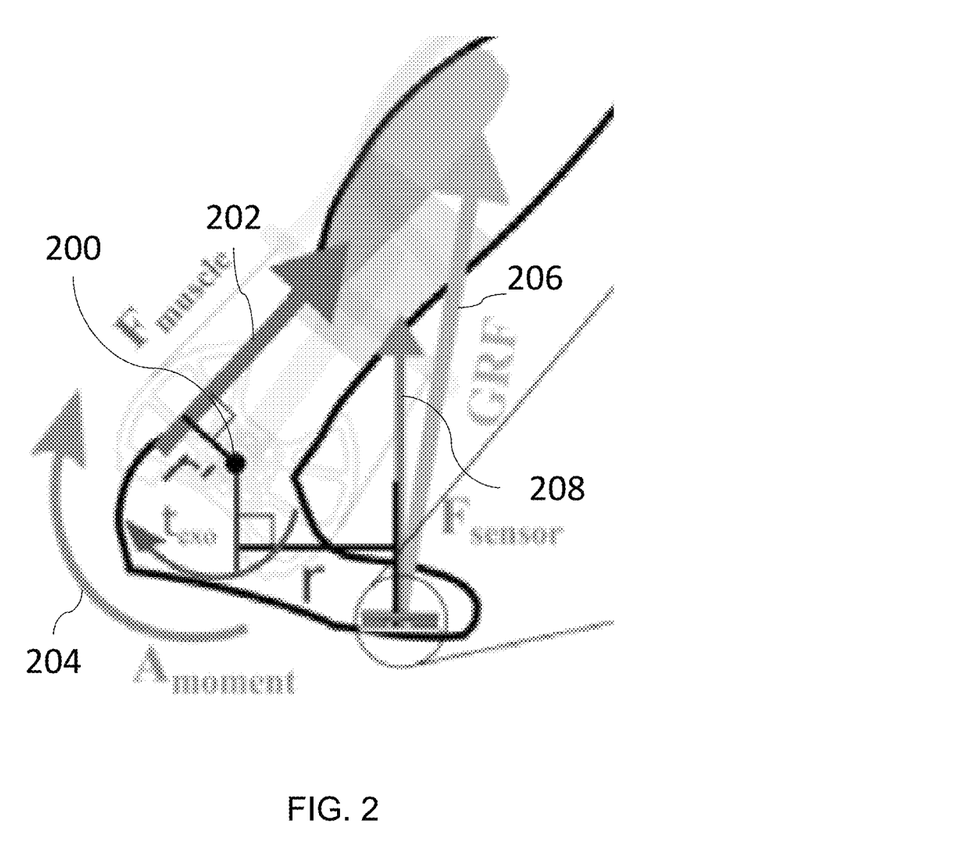
FIG. 2 shows a schematic depiction of a torque balance around an ankle joint.

FIG. 2 is an illustrative torque balance diagram of forces which may occur around an ankle joint 200. A leg muscle may generate a muscle force 202. The muscle force 202 may be applied around ankle joint 200 axis to produce ankle moment 204. A foot may produce ground reaction force 206 against a walking surface, which may counterbalance ankle moment 204. Ground reaction force 206 may be measured by one or more sensors (e.g. sensor 102 in FIG. 1) to yield sensor force 208. Sensor force 208 may be approximately proportional to a normal component of ground reaction force 206.

Sensors (e.g. sensor 102 in FIG. 1) may be designed according to a specification necessary to measure an appropriate sensor force (e.g. sensor force 208) in order to estimate a joint (e.g. ankle, knee, hip) moment in real-time. Sensor may be positioned between a user's foot and a ground surface, to measure forces between the foot and the ground (e.g. ground reaction force 206). Sensor force (e.g. 208) measurement may be used as an initial input signal for controlling an assistive device (e.g. assistive device 100 in FIG. 1). One or more sensors may be disposed on an assistive device. A sensor may be incorporated into a force sensing assembly or housing.

Figure 3:
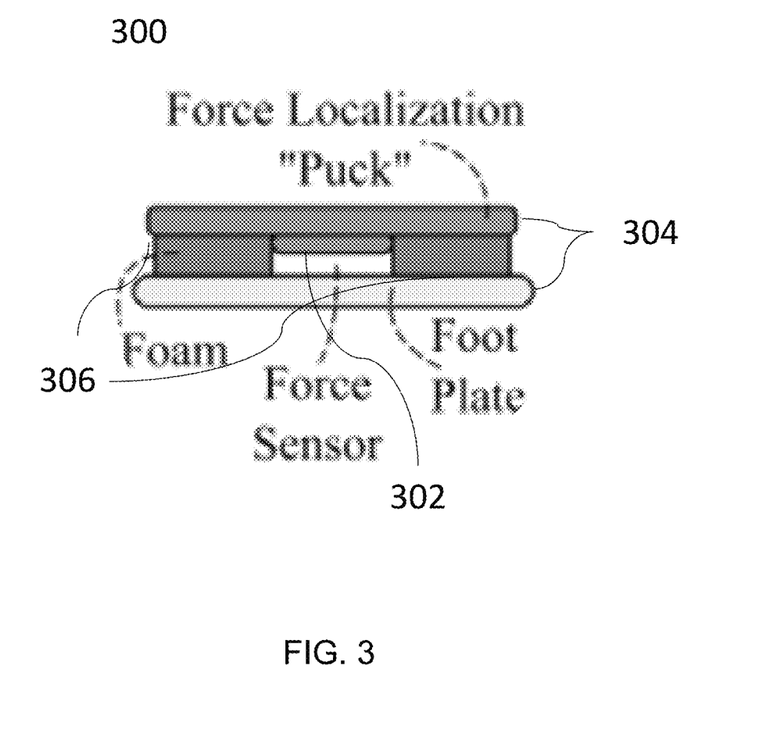
FIG. 3 shows a schematic depiction of a force sensor apparatus.

FIG. 3 is a diagram of an embodiment of force sensing assembly 300. Force sensing assembly 300 may include force sensor 302. Above and/or below force sensor 302 may be plates 304, which may serve to distribute forces from a wider area than the area of the sensor 302 alone. Sensor 302 may be mounted to top plate of plates 304, while the bottom plate of plates 304 may be part of a foot plate that is connected to an orthosis and arranged to be positioned underneath a foot of the user. The plates may be rounded to localize or distribute the force on the force sensor. Around sensor 302 and between plates 304 may be a layer of foam 306 (e.g. neoprene foam), which may serve to balance and distribute the forces from the plates 304 across the sensor 302. Of the plates 304, one plate may be positioned towards a foot of a user and, and another plate of plates 304 may be positioned towards a ground surface (e.g. positioned against an insole of a shoe).

Figure 4:
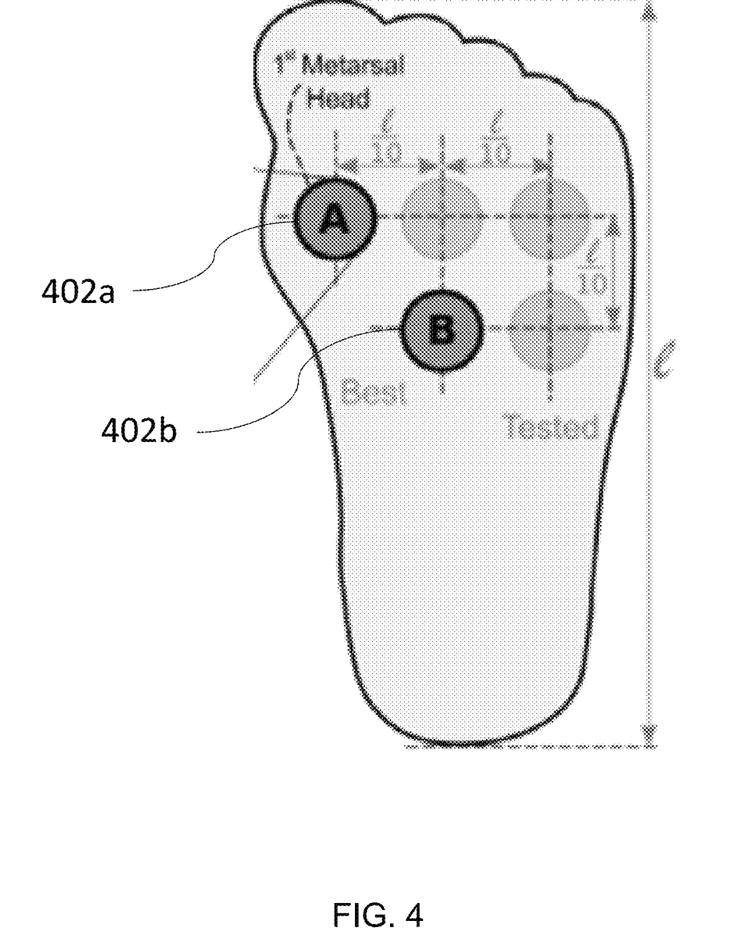
FIG. 4 shows a schematic depiction of foot sensor locations.

FIG. 4 shows a diagram of example placements of force sensing assemblies 402 relative to a bottom surface of a foot of a user or relative to a top surface of an orthotic insert foot plate. Force sensing assemblies may be attached to a foot plate by a sensor assembly plate (e.g. plate 304 in FIG. 3). A first force sensing assembly 402a may be placed in a first location to sense a first spatial component of a force applied by a foot against a ground surface. A second force sensing assembly 402b may be placed in a second location to sense a second spatial component of a force applied by a foot against a ground surface. Two or more force sensing assemblies 402 may be used in order to allow for a ratio of forces to be measured, as a method to infer a spatial distribution of weight across a foot or a center of pressure across a foot. Sensors may be placed in any of a number of placement locations. An example arrangement yielding high prediction accuracy may include a sensor placed directly under a head of a first metatarsal bone (location of 402a) and another placed along a path of a center of pressure (location of 402b).

A purpose of force sensors (e.g. sensor 102 in FIG. 1) may be to provide force information which may be used to infer gait an intention of a user, and thereby inform assistive device to provide assistive torque at appropriate timing and intensity to intuitively assist a user. A force sensor may provide an input for a proportional joint-moment control method.

Figure 5:
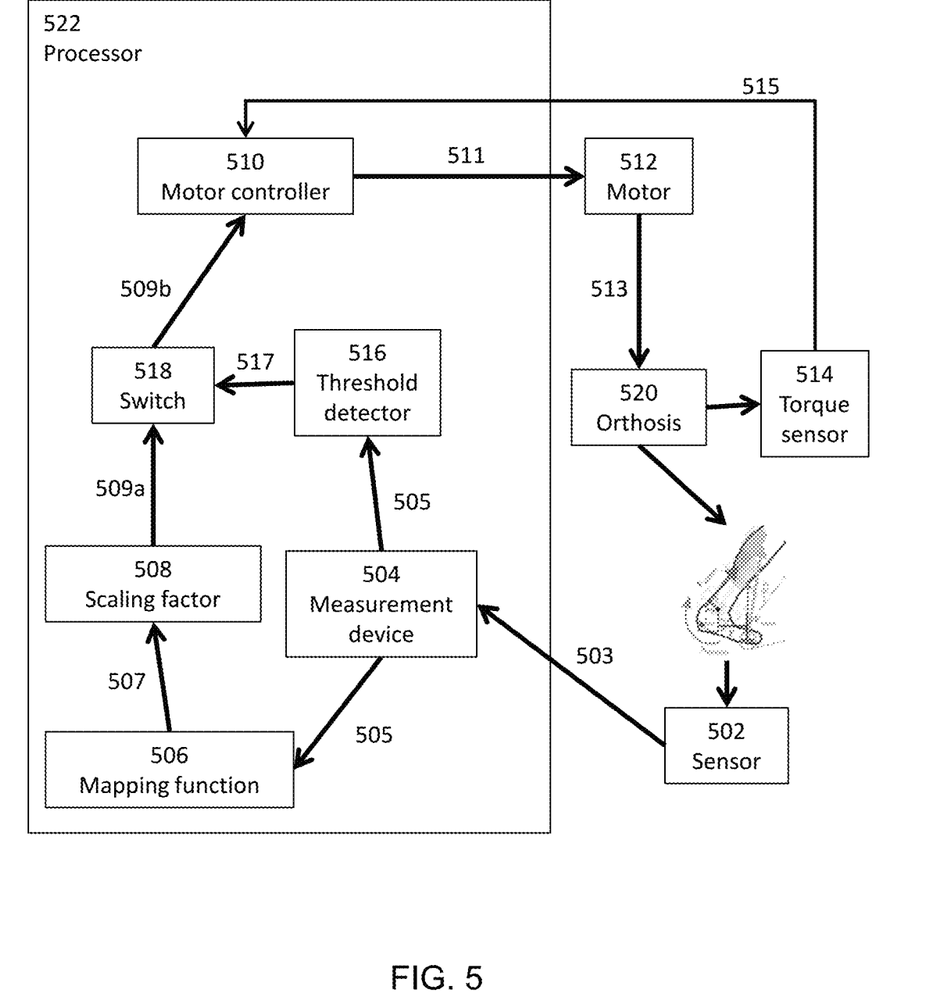
FIG. 5 shows a system block diagram of an implementation of proportional joint-moment control within an assistive exoskeleton

FIG. 5 shows an example component diagram of a system for proportional control of assistive device (e.g. assistive device 100 in FIG. 1) (e.g. an ankle exoskeleton assistive device). The system includes orthosis 520 configured to be worn by a user. Motor 512 is controlled by motor controller 510 to apply torque force to orthosis 520. To control the amount of force applied to orthosis 520 by motor 512, system includes processor 522. Processor 522 (e.g. an ARM chip, a microcontroller) may comprise a computer having input, output, memory storage, and processing capabilities. Processor 522 is configured to receive data from one or more sensors 502 coupled to the orthosis and to process the received data to determine an appropriate motor controller 510 output.

Sensor 502 may be disposed on assistive device (e.g. a force sensor against a foot or inside a shoe, e.g. sensor 102 on assistive device 100 in FIG. 1). Sensor 502 may produce electrical signals 503 which may be proportional to a measured parameter (e.g. force, pressure, torque, acceleration) of sensor 502. Sensor 502 may be configured in the same manner as sensor assembly 300 shown in FIG. 3. Sensor 502 may transmit electrical signals 503 to an input of a measurement device 504, which may comprise a processor 522. Measurement device 504 may interpret sensor electrical signal 503 received from sensor 502 as measured force 505, which generally measures the force at which the foot is pressing upon a ground surface, which may, in turn, include forces generated by a user and forces generated by assistive device (e.g. assistive torque 513). Measured force 505 may then be processed with or without a mapping function 506 to estimate user-generated torque 507. A mapping function 506 may be a mathematical function (e.g. second-order polynomial, exponential, linear) which may serve to convert a measured force 505 into an estimated torque 507 at the wearer's ankle join. Approaches for implementing mapping function 506 are described in more detail below. Mapping function 506 may be generated by a curve fitting of an experimental calibration data set with measured values of sensor force (e.g. sensor force 208 in FIG. 2) and estimated user applied torque (e.g. estimates of ankle moment 204 in FIG. 2). A mapping function 506 may be any arbitrary function or lookup table, and an estimated user-generated torque 507 need not correspond to a true user-generated torque.

Estimated user-generated torque 507 may be multiplied by scaling factor 508 to determine desired assistive torque 509. Scaling factor 508 may be a percentage factor (e.g. 50%), such that a desired assistive torque 509 is, e.g., 50% of an estimated user-generated torque 507. The user may select or adjust scaling factor 508. In general, scaling factor 508 is selected based on the user's desired level of assistance. A user may select or adjust scaling factor 508 at any time while wearing an assistive device, such as when donning a device for a session.

The desired assistive torque 509 may be passed to motor controller 510 (e.g. a proportional-integral-derivative (PID) feedback motor controller). In turn, motor controller 510 sends motor instructions 511 to one or more motor 512 to cause motor 512 to apply assistive torque 513 to a body of a user (e.g. assistive ankle torque), where a magnitude of the assistive torque 513 is approximately equal to desired assistive torque 509, such as by applying force through orthosis 520 (e.g. a foot plate orthotic insert).

Orthosis 520 may include torque sensor 514 configured to measure assistive torque 513 applied to orthosis 520 by motor 512. Torque sensor 514 is also configured to send a torque output measurement 515 to motor controller 510. Torque output measurement 515 may allow feedback control (e.g. PID control) by motor controller 510, so as to match a magnitude of assistive torque 513 applied to orthosis 520 to magnitude of desired assistive torque 509. A torque output measurement 515 may be sent to motor controller 510 via processor 522.

Feedback control (e.g. PID control) may be used in a condition where desired assistive torque is equal to zero torque. Under such a condition, feedback control may serve to compensate for passive forces (e.g. motor inertia, transmission cable friction) of an assistive device which may serve to inhibit a user's movement. Feedback control may produce output forces from motors 512 configured so that torque sensor 514 reads substantially zero torque.

A user may desire to have assistive torque 513 reduced to zero during certain movements (e.g. when a foot is off the ground, as during swing phase of gait). For example, the user may desire to have assistive torque 513 set to a specific value during certain movements (e.g. a dorsiflexion assistive torque to correct for a foot drop or a toe drag during swing phase).

Setting a zero-torque or dorsiflexion-torque during certain gait states may comprise a modification to the proportional joint-moment control algorithm and the system depicted in FIG. 5. Such a modification may be accomplished by a switch (e.g. switch 518) that is configured to selectively modify the operation of motor controller 510 and, thereby the application of assistive force to orthosis 520. Desired assistive torque 509 may be passed through switch 518, such that a desired assistive torque 509 may comprise a pre-switch 518 desired assistive torque 509a and a post-switch desired assistive torque 509b. With switch 518 in a first state or condition, pre-switch desired assistive torque 509a may be substantially equal to post-switch desired assistive torque 509b. But with switch 518 in a second state or condition, post-switch desired assistive torque 509b may be significantly attenuated as compared to pre-switch desired assistive torque 509a or post-switch desired assistive torque 509b may have a value of zero. The state or condition of switch 518 may be controlled by an estimated gait state input, such as gait state 517 produced by threshold detector 516.

Threshold detector 516 is configured to process a received input signal (e.g., measured force 505, user generated torque 507) to determine gait state 517. If the magnitude of the received input signal is below a threshold value (indicating that the user is not in a portion of the gait in which significant forces are being applied to the user's orthosis 520 and may not require assistance), the gait state 517 may be set to a value that causes switch 518 to attenuate (or set to zero) the magnitude of post-switch desired assistive torque 509b. Conversely, if the magnitude of the received input signal is above a threshold value (indicating that the user is in a portion of the gait in which significant forces are being applied to the user's orthosis 520), the gait state 517 may be set to a value that causes switch 518 to not attenuate or otherwise modify the magnitude of post-switch desired assistive torque 509b.

Threshold detector 516 may be memoryless or may have memory, and may act as a state machine. Threshold detector 516 may operate to distinguish multiple gait states, including swing phase, early stance phase, and late stance phase. In some embodiments, threshold detector 516 may produce an output corresponding to a gait state 517 that may encode several different states that may occur throughout an individual's gait cycle (e.g. stance, initial contact, swing). In that case, switch 518 may gate pre-switch desired assistive torque 509a, such that when the switch 508 is in an active state (e.g. when a gait state 517 encodes a stance phase) post-switch desired assistive torque 509b may be equal to the pre-switch desired assistive torque 509a, and when switch 508 is in an inactive state (e.g. when gait state 517 encodes a swing phase) post-switch desired assistive torque 509b may equal to zero torque or may be equal to a small torque (e.g. a small dorsi-flexion torque to prevent toe drag).

Threshold detector 516 and switch 518 may each be implemented as discrete processes or circuits on processor 522.

As described above, mapping function 506 operates to translate a measured force (e.g., from sensor 502) into an approximation of the force moment at the user's joint (e.g. ankle moment 204 in FIG. 2). The estimated force moment is then used to determine how much assistance to be provided to the user through orthosis 520 via the application of force by motor 512. Because the relation between sensor force (e.g. measured force 505) and biological joint torque (e.g. ankle moment 204 in FIG. 2) is at least partially determined by the individual attributes of the user (e.g., the length of the user's foot, which affects the distance between the ankle joint and sensor 502), a process may be used to adjust mapping function 506 for a particular user. Note that herein the term "adjust" may refer to a user-specific modification of a mapping function 506, while the term "calibrate" may refer to an initial generation of a mapping function 506 (e.g. using paired data, such as sensor readings paired to optical motion tracking with inverse dynamics).

An initial calibration process may be performed by an individual user wearing a force sensor (e.g. force sensors 502 of FIG. 5) while walking, with or without powered assistance, across a varying speed profile on a treadmill while collecting gait kinematics and kinetics (e.g., by treadmill force sensors or optical motion capture). An example calibration may include three separate acceleration trials (0.25, 0.125, and 0.083 m/s$^2$), with a treadmill increasing speed from 0 m/s to 1.25 m/s, then, following 10 seconds at constant speed, returning to 0 m/s. Gait analysis and biomechanical modeling may be used to compute a biological ankle moment (e.g. ankle moment 204 of FIG. 2) via an inverse dynamics calculation using the collected kinematic and kinetic data.

In some embodiments, any of mapping function 506, threshold detector 516, switch 518, and scaling factor 508 may be merged into a combined function. The combined function may map directly from measured force 505 to desired assistive torque 509. The combined function may incorporate a low-input response (e.g. dorsiflexion during swing phase) as a component of its output.

Figure 6A:
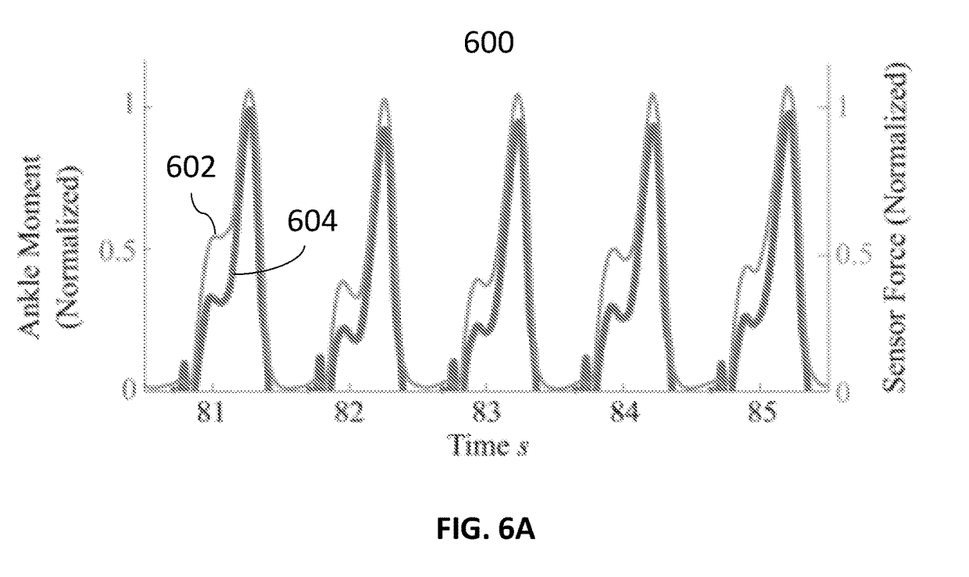
FIG. 6A shows a comparison of an estimated biological ankle moment and a measured sensor force during a calibration procedure.

FIG. 6A shows an example trace of calibration data 600 generated during a calibration experiment. A calibration experiment may comprise a participant walking at steady state while wearing a force sensor (e.g. force sensor 300 in FIG. 3) and while undergoing motion tracking. An estimation of a biological joint moment (e.g. ankle moment 204 in FIG. 2) may be performed by acquiring motion tracking of a participant, followed by a computer simulation of joint forces based on the motion tracking. A motion tracking and simulation system may estimate a biological joint (e.g. ankle, knee, hip) moment 602. Simultaneously, a force sensor may track a measured force 604 (e.g. measured force 208 in FIG. 2).

Figure 6B:
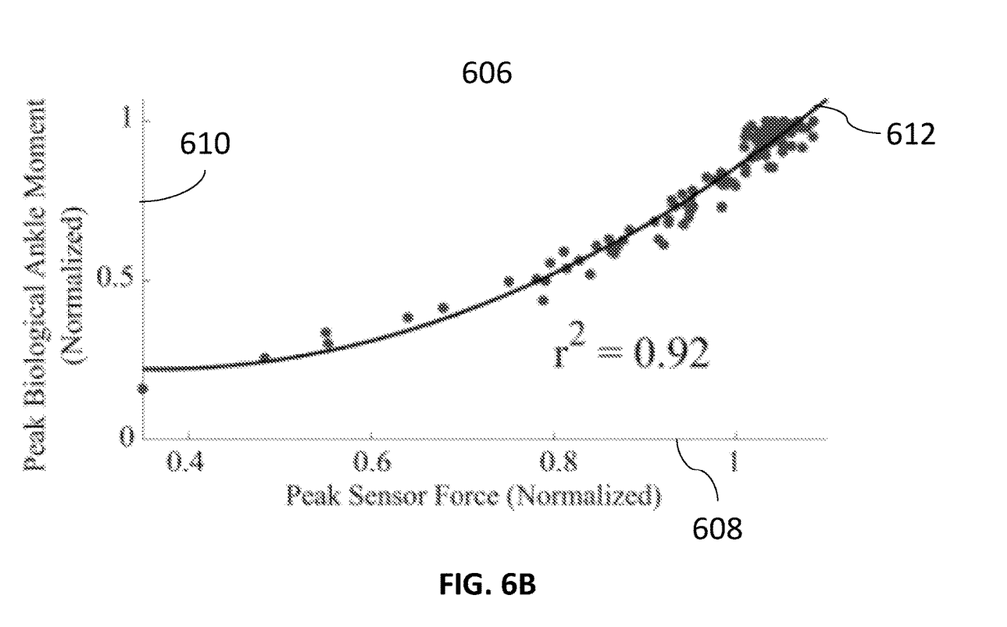
FIG. 6B shows a scatter plot and second order polynomial regression describing the relationship between peak normalized ankle moment and peak normalized sensor force during a calibration procedure.

FIG. 6B shows a calibration plot 606. A calibration plot 606 may compare a peak force sensor reading 608 (e.g. peak readings of measured force 604) to a peak joint moment 610 (e.g. peak estimates of biological ankle moment 602), as acquired during a test with a participant walking. This data may be fit by a curve equation 612 (e.g. a second-order polynomial equation)

An equation may be used to relate an instantaneous foot sensor force to a corresponding instantaneous ankle joint moment. Such an equation may normalize an instantaneous foot sensor force reading ($F_{sen}$) by an average peak foot sensor force reading during a steady-state preferred walking speed baseline calibration period (e.g 5 seconds) ($F_{ref}$). The baseline calibration period may take place again after operation of proportional joint-moment control to re-establish the baseline foot sensor force during walking with assistance. A normalization may yield an instantaneous foot sensor force ratio ($R_F = F_{sen}/F_{ref}$). The relationship between peak values of a measured foot sensor force ratio ($R_F$) and peak values of a normalized biological ankle moment may be related using a 2nd order polynomial regression. An example regression is shown in FIG. 6B, having $r^2=0.92$ and an equation as follows:

$$M_{bio} = 1.55 R_F^2 - 1.12 R_F + 0.42 \qquad \text{Equation (1)}$$

where $M_{bio}$ represents the estimated ankle moment normalized by the peak ankle moment at preferred speed. Such an equation may subsequently be used to infer a joint moment (e.g. ankle, knee, hip; e.g. ankle moment 204 in FIG. 2) from a sensor reading (e.g. a foot force sensor; e.g. sensor force 208 in FIG. 2). Accordingly, Equation (1) may be incorporated into mapping function 506 of FIG. 5 and operate as the mechanism to translate the force measurement received from sensor 502 into user-generated torque 507.

A calibration data set, such as the data set used to generate Equation (1), may include data from one or more individuals and may include data from individuals having one or more motor impairments. Mapping function 506 may comprise an equation, such as Equation (1), which may convert from a sensor reading (e.g. measured force 208 in FIG. 2) into an estimated biological joint torque (e.g. ankle moment 204 in FIG. 2). Mapping function 506 may comprise a lookup table, which may serve as an arbitrary function mapping an input to an output. A lookup table may be generated directly from a calibration data set, such as by averaging the output values (e.g. $M_{bio}$) measured for each input value (e.g. $R_F$). A lookup table may use an interpolation method (e.g. linear interpolation, spline interpolation) to infer an output when given an input which is between two input values explicitly included in the lookup table. A lookup table may use an extrapolation method (e.g. linear extrapolation, polynomial extrapolation) when given an input which is below the minimum input or above the maximum input, A proportional joint-moment control method may be incorporated within a real-time or substantially real-time exoskeleton control scheme. Operation of a controller may require a brief (e.g. 5 second) adjustment procedure to determine $F_{ref}$ (foot sensor force reference) during steady-state walking, and a user's preferred torque magnitude (two) at that speed. For example, a user may prefer 0.3 Nm/kg of peak exoskeleton torque while walking at their preferred speed of 1.2 m/s. During operation of a controller following an adjustment procedure, exoskeleton assistance torque (t) may be provided according to the ratio of the instantaneous estimated joint moment $M_{bio}(t)$ relative to the estimated joint moment during walking at steady-state ($M_{bio,ss}$), as in Equation (2):

$$\text{Torque}(t) = t_{v0} \frac{Mbio(t)}{Mbio, SS} \qquad \text{Equation (2)}$$

where $M_{bio,SS}$ is a constant that may account for a relationship between a foot sensor force ratio ($R_F$) and a normalized biological ankle moment at the preferred speed. As a result of Equation (2), a specified exoskeleton torque may adapt instantaneously (e.g. in less than 10 ms) to a demand placed on a biological joint during a weight bearing task by prescribing assistance as a percentage of an estimated moment. Following estimation of the ankle moment and prescription of assistance based on Equation (2), low level torque feedback motor control may be used to produce a desired instantaneous assistive torque profile.

Figure 7:
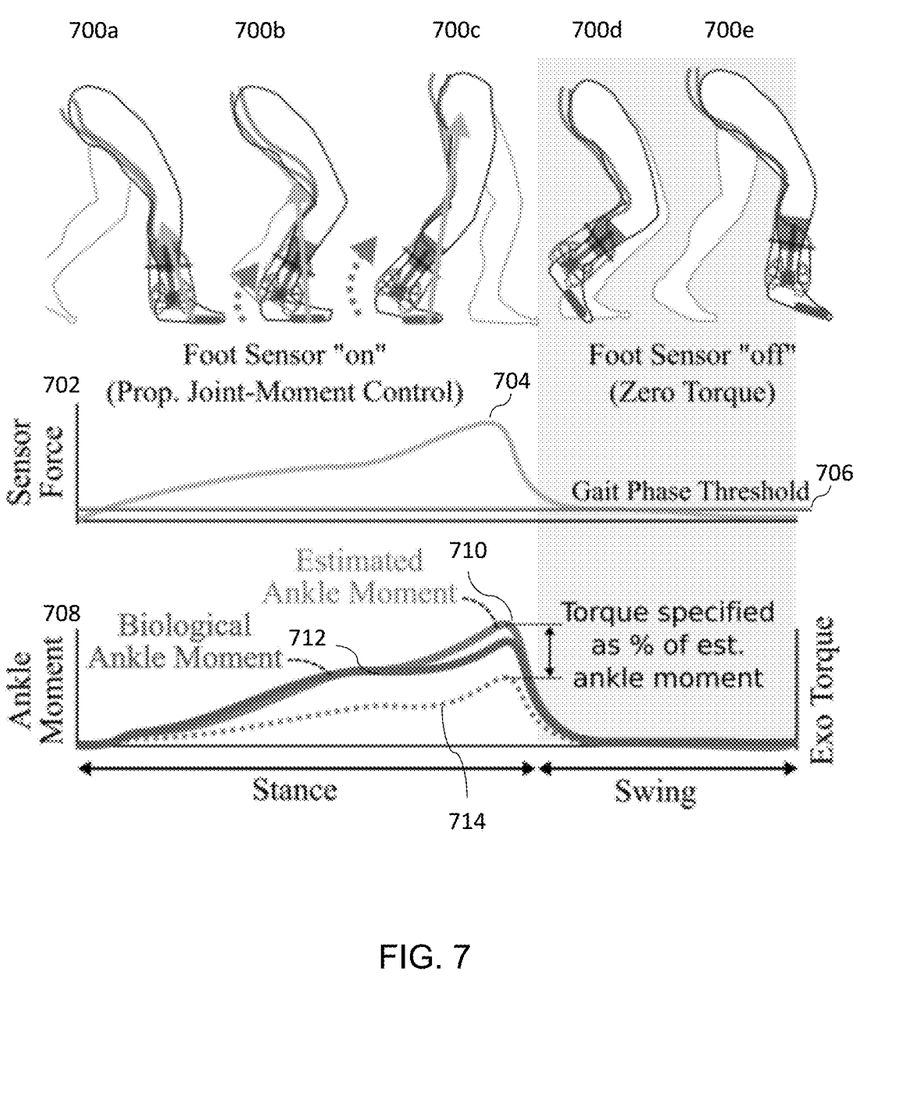
FIG. 7 shows a depiction of proportional assistance levels through a gait cycle.

FIG. 7 shows an example of an assistive torque profile through a gait cycle of a user 700a-700e, though a single step, with an attached assistive exoskeleton (e.g. an ankle exoskeleton). Gait cycle positions 700a-700c may be herein referred to as "stance phase", and gait cycle positions 700d and 700e may be herein referred to as "swing phase". Plot 702 depicts a sensor force reading 704 through a gait cycle. During swing phase, the foot sensor reading may be below a threshold 706. When a foot sensor 704 reading is below a threshold 706, a controller may determine that a leg is in swing phase and may assign zero torque output (rather than proportional torque output). Plot 708 depicts an exoskeleton assistive torque applied by a controller through a gait cycle. An estimated ankle moment 710 may be generated based on a force sensor reading. An estimated ankle moment may be configured to approximately correspond to a biological ankle moment 712. A desired assistive torque 714 may be generated as a scaled version of an estimated ankle moment 710. A threshold 706 may be additionally incorporated into the generation of the desired assistive torque 714. In some embodiments, a desired assistive torque 714 may be generated directly from a force sensor reading, without an intermediate estimated ankle moment 710. In some embodiments, a controller may comprise both a threshold 706 and a state machine, in order to classify a gait cycle of a user (e.g. swing or stance). In some embodiments, a controller may use no threshold. In an embodiment, a desired assistive torque 714 may include a dorsiflexion assistance to prevent foot drop during a swing phase, with the swing phase determined by a controller (e.g., by a threshold, by a threshold and state machine, or directly from a force reading 704)

A proportional joint-moment control scheme may be implemented on an assistive exoskeleton (e.g. an untethered battery-powered and wireless robotic ankle exoskeleton). An exoskeleton may be designed to minimize a metabolic burden of adding mass to a lower-extremity by placing motors and battery at the waist. Bowden cables may transmit torque from DC motors to fitted ankle-foot assemblies. In an embodiment, ankle-foot assemblies may be composed of aluminum sheet-metal or carbon fiber insoles, torque sensors, torque transmission pulleys, Bowden cable attachment points, aluminum bar-stock or carbon fiber lateral supports, and plastic-molded or carbon fiber calf attachments. A foot plate assembly may articulate in the sagittal plane in order to provide plantar-flexion and dorsi-flexion assistance. Torque sensors mounted at the ankle joint and proportional-integral-derivative (PID) motor control may be used to track an instantaneous torque profile.

Figure 8:
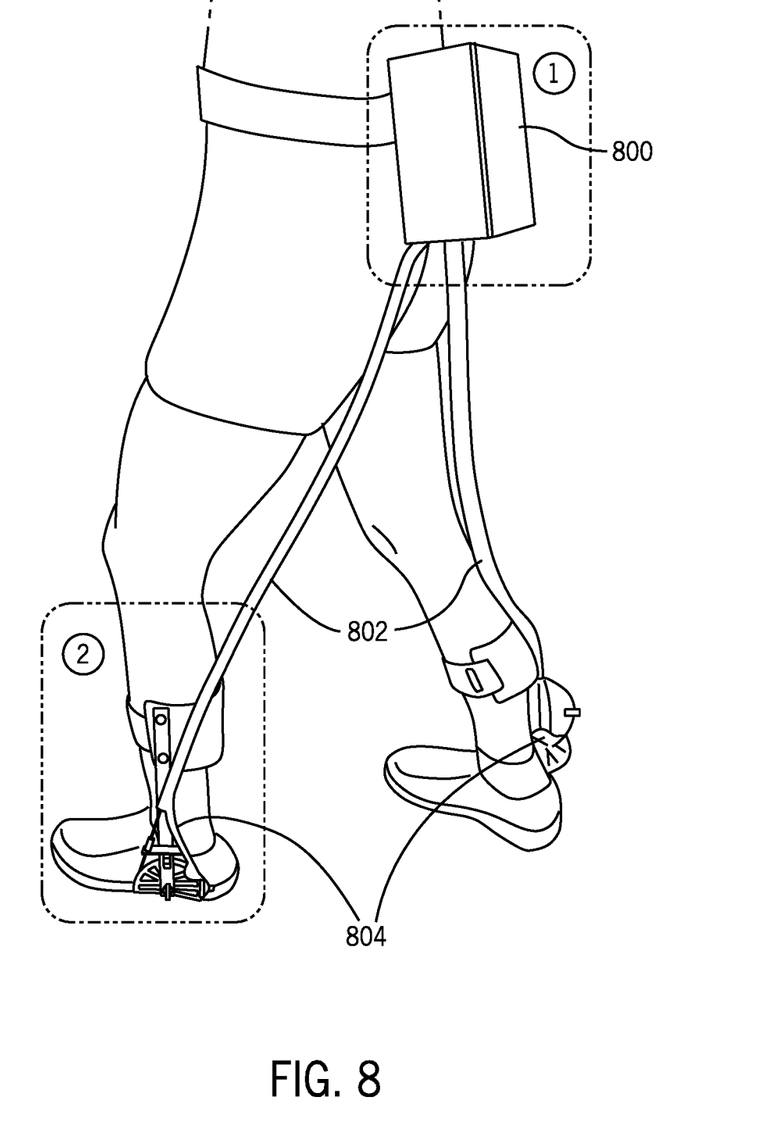
FIG. 8 shows an example embodiment of an assistive exoskeleton.

FIG. 8 shows an example ankle exoskeleton. An ankle exoskeleton may be comprised of a control and actuation assembly 800 placed above a user's waist, an ankle assembly 804 attached around a user's ankle joint to apply assistive torque, and a Bowden cable transmission 802 to transfer power from the control and actuation assembly 800 to the ankle assembly 804.

By adapting to the dynamics of biological joints in real-time, a controller may, in effect, sense a net result of the neural commands. An advantage of proportional control strategies, like proportional joint-moment control, is that they may not require additional controller adjustments for unique and asymmetric pathological gait patterns.

The proportional joint-moment controller described herein may be well suited for real-world application and adoption. Because force sensors for proportional joint-moment control may be embedded in an exoskeleton's foot plates, no addition sensors, components, or adjustments may be needed once an exoskeleton has been fitted to the user, resulting in minimal set-up time and low burden of use. Proportional joint-moment control may be intuitive and simple to understand for young or cognitively impaired participants. Proportional joint-moment control may allow for direct user input and testing (i.e., pressing harder will increase assistance, and vice-versa). Exoskeleton adjustment may be quickly and easily self-implemented; upon donning a device each session, a user may simply tune the amount of assistance to the user's preference while walking at normal speed. A user may walk for a period of time (e.g. 60 seconds) at a preferred speed (v0) to establish a preferred torque magnitude at that speed ($t_{v0}$) and adjust the processing (e.g. mapping function 506, scaling factor 508, threshold detector 516 from FIG. 5) to obtain the desired assistance given the reference estimated joint moment during walking at steady-state ($M_{bio,ss}$).

The described features, advantages, and characteristics may be combined in any suitable manner in one or more embodiments. One skilled in the relevant art will recognize that the circuit may be practiced without one or more of the specific features or advantages of a particular embodiment. In other instances, additional features and advantages may be recognized in certain embodiments that may not be present in all embodiments.

Reference throughout this specification to "one embodiment," "an embodiment," or similar language means that a particular feature, structure, or characteristic described in connection with the embodiment is included in at least one embodiment. Thus appearances of the phrase "in one embodiment," "in an embodiment," and similar language throughout this specification may, but do not necessarily, all refer to the same embodiment.

I claim:

1. A device, comprising:
    an orthosis configured to couple to a leg of a user, the orthosis including a first part configured to couple to the lower leg of the user, a second part configured to be arranged below the user's foot, and a rotational assembly between the first part and second part;
    a pressure sensor coupled to the second part and configured to be positioned underneath a foot of the user when the orthosis is coupled to the leg of the user,
    a motor configured to apply a force to the orthosis to generate a torque force between the first part and the second part; and
    a processor, the processor being configured to:
        receive an instantaneous force measurement value from the pressure sensor, the instantaneous force measurement value reflecting an amount of force being exerted by the user's foot against the second part when the second part is in contact with the ground,
        determine, a desired assistive torque value as a function of the instantaneous force measurement value by estimating, based on the instantaneous force measurement value, a user-generated biological torque applied by the user at the ankle of the user between the user's lower leg and the user's foot when the user's foot is pressing against the ground; and
        multiplying the estimate of user-generated biological torque by a scaling factor to determine the desired assistive torque value, and
        operate the motor to cause the motor to apply a force to the orthosis to generate a torque force between the first part and the second part equal to the desired assistive torque value
    wherein, estimating the user generated biological torque comprises:
        normalizing the instantaneous force measurement value by an average of peak force measurement values recorded by the pressure sensor while the user is walking for a predetermined calibration period, and applying the normalized instantaneous pressure measurements to a mapping function relating normalized instantaneous pressure measurements to estimates biological ankle moment.

2. The device of claim 1, wherein the processor is configured to:
    compare the instantaneous force measurement value received from the pressure sensor to a threshold; and
    when the instantaneous force measurement value is less than the threshold, set the desired assistive torque value to a minimum torque value.

3. The device of claim 1, further comprising a torque sensor coupled to the orthosis, wherein the torque sensor is configured to measure a magnitude of the torque force generated by the motor.

4. The device of claim 3, wherein the processor is configured to receive the measured magnitude of the torque force from the torque sensor and modify an operation of the motor based upon the magnitude of the torque force.

5. The device of claim 1, wherein the second part comprises a foot plate configured to be positioned underneath the foot of the user and the pressure sensor is coupled to the foot plate.

6. The device of claim 5, wherein the pressure sensor is mounted to a first plate over the foot plate and further comprising a layer of foam disposed between the first plate and the foot plate.

7. The device of claim 1, wherein the peak force measurement values recorded by the pressure sensor while the user is walking for a determined calibration period are taken at a user's preferred speed, while the device is providing a predetermined level of assistance, during the predetermined calibration period.

8. The device of claim 1, wherein the mapping function relates normalized instantaneous pressure measurements to estimates of biological ankle moment normalized by estimates of peak biological ankle moment.

9. The device of claim 1, wherein the processor is configured to: compare the instantaneous force measurement value received from the pressure sensor to a threshold; and when the instantaneous force measurement value is less than the threshold, set the desired assistive torque value to a negative torque value such that torque is provided that resists rotation of the second part relative to the first part.

10. A device, comprising:
    an orthosis configured to couple around a body joint of a user, wherein the orthosis is configured to be coupled to a first body part on a first side of the joint and a second body part on a second side of the joint,
    a pressure sensor coupled to the orthosis and configured to measure force being exerted by the user through the second body part on the orthosis when the orthosis is resisting rotation,
    a motor configured to apply a force to the orthosis to generate a torque force across the joint of the user; and
    a processor, the processor being configured to determine, on the basis of an instantaneous force measurement received from the pressure sensor, a desired torque value by normalizing the instantaneous force value by an average of peak force measurement values recorded by the pressure sensor when the user is actuating the orthosis during a predetermined calibration period; and multiplying the normalized instantaneous force value by a scaling factor to determine the desired assistive torque value, and operate the motor based on the desired torque value.

11. The device of claim 10, wherein the processor is configured to:

compare the instantaneous force measurement value received from the pressure sensor to a threshold; and when the instantaneous force measurement value is less than the threshold, set the desired assistive torque value to a minimum torque value.

12. The device of claim 10, further comprising a torque sensor coupled to the orthosis, wherein the torque sensor is configured to measure a magnitude of the torque force generated by the motor; and wherein the processor is configured to receive the measured magnitude of the torque force from the torque sensor and modify an operation of the motor based upon the magnitude of the torque force.

13. The device of claim 10, wherein the orthosis includes a first plate configured to be positioned against the body part of the user and the pressure sensor is operable to measure compressive force exerted on the first plate; and wherein the pressure sensor is mounted to a second plate beneath the first plate and further comprising a layer of foam disposed between the first plate and the second plate.

14. The device of claim 10, wherein the joint is a knee joint.

15. The device of claim 10, wherein the joint is a hip joint.

16. A method of applying assistive force with an orthosis, comprising:

receiving an instantaneous force measurement from a pressure sensor, wherein the pressure sensor is configured to measure an instantaneous force applied by a body part of a user, to produce an instantaneous force measurement value;

determining, as a function of the instantaneous force measurement value, a desired assistive torque value by estimating, based on the measurement of body force, a user-generated biological torque at the biological joint of the user, when the user-generated biological torque is being resisted; and multiplying the user-generated torque by a scaling factor to determine the desired assistive torque value; and, operating a motor to cause the motor to apply a motor force to the orthosis to generate a motor torque force across the joint equal to the desired assistive torque value wherein estimating the user generated biological torque at the biological joint of the user comprises:

normalizing the instantaneous force measurement by an average of peak force measurement values recorded by the pressure sensor while the user is actuating the orthosis for a predetermined calibration period, and applying the normalized instantaneous pressure measurements to a mapping function relating normalized instantaneous pressure measurements to estimate user generated biological torque.

17. The method of claim 16, wherein the method further comprises:

comparing the instantaneous force measurement value to a threshold; and when the instantaneous force measurement value is less than the threshold, setting the desired assistive torque value to a minimum torque value.

18. The method of claim 17, wherein the method further comprises:

receiving from the user a scaling factor setting; and modifying the scaling factor according to the scaling factor setting.

19. The method of claim 16, wherein the method further comprises:

measuring, using a torque sensor, a magnitude of the torque force applied across the joint by the motor; and modifying an operation of the motor based upon the magnitude of the torque force.

* * * * *

UNITED STATES PATENT AND TRADEMARK OFFICE
CERTIFICATE OF CORRECTION

| | | |
|---|---|---|
| PATENT NO. | : 11,622,905 B2 | Page 1 of 1 |
| APPLICATION NO. | : 16/403121 | |
| DATED | : April 11, 2023 | |
| INVENTOR(S) | : Zachary F. Lerner | |

It is certified that error appears in the above-identified patent and that said Letters Patent is hereby corrected as shown below:

In the Specification

Column 9, Line 47, "(two)" should be --($t_{v0}$)--.

Signed and Sealed this
Sixteenth Day of April, 2024

Katherine Kelly Vidal
*Director of the United States Patent and Trademark Office*